(12) United States Patent
de la Huerga

(10) Patent No.: US 6,345,268 B1
(45) Date of Patent: Feb. 5, 2002

(54) METHOD AND SYSTEM FOR RESOLVING TEMPORAL DESCRIPTORS OF DATA RECORDS IN A COMPUTER SYSTEM

(76) Inventor: Carlos de la Huerga, 9190 N. Upper River Rd., River Hills, WI (US) 53217

( * ) Notice: Subject to any disclaimer, the term of this patent is extended or adjusted under 35 U.S.C. 154(b) by 0 days.

(21) Appl. No.: 09/130,934

(22) Filed: Aug. 7, 1998

Related U.S. Application Data

(63) Continuation-in-part of application No. 08/871,818, filed on Jun. 9, 1997, now Pat. No. 5,903,889.
(60) Provisional application No. 60/054,923, filed on Aug. 8, 1997.

(51) Int. Cl.[7] .......................... G06F 17/30; G06F 17/60; G06F 15/16
(52) U.S. Cl. ............................. 707/3; 707/10; 707/102; 707/104; 705/2; 705/3; 709/217; 709/218
(58) Field of Search ........................ 705/2, 3, 4; 707/3, 707/4, 5, 10, 102, 104; 709/217, 218

(56) References Cited

U.S. PATENT DOCUMENTS

| | | | | |
|---|---|---|---|---|
| 3,872,448 A | * | 3/1975 | Mitchell, Jr. .................. | 705/3 |
| 4,817,050 A | * | 3/1989 | Komatsu et al. ............... | 707/10 |
| 4,878,175 A | * | 10/1989 | Norden-Paul et al. ......... | 705/2 |
| 4,893,270 A | * | 1/1990 | Beck et al. .................... | 700/90 |
| 4,958,283 A | * | 9/1990 | Tawara et al. ............... | 382/131 |
| 5,065,315 A | * | 11/1991 | Garcia ........................... | 705/2 |
| 5,146,439 A | * | 9/1992 | Jackmann et al. ............. | 369/25 |
| 5,361,202 A | * | 11/1994 | Doue ............................ | 705/3 |
| 5,903,889 A | * | 5/1999 | De La Huerga et al. ........ | 707/3 |

* cited by examiner

*Primary Examiner*—Thomas Black
*Assistant Examiner*—Frantz Coby
(74) *Attorney, Agent, or Firm*—Michael A. Jaskolski; Quarles & Brady, LLP

(57) ABSTRACT

A computer system for use in hospitals and the like to automate the referencing, locating, and retrieving of data records according to temporal descriptors. The temporal descriptors identify the date and time of creation of data records sought to be retrieved, and may do so by referring to a particular event known to have occurred at a particular date and time (e.g., a patient's admission to the hospital). The temporal descriptors may be used in a simple query for a data record, or they may be used within data records to refer to other data records. In either case, a system user can select one or more data records referred to by the temporal descriptors wherein selection criteria include information such as date and time ranges and other instructions for electing data records.

53 Claims, 2 Drawing Sheets

| Temporal Descriptor Definition | |
|---|---|
| Temporal Descriptors | Time Range & Instructions |
| Admission | Time Range Before Admission Time Acceptable |
| | Time Range After Admission Time Acceptable |
| | Instructions for Selecting Appropriate Record(s) |
| Discharge | Time Range Before Discharge Time Acceptable |
| | Time Range After Discharge Time Acceptable |
| | Instructions for Selecting Appropriate Record(s) |
| Descriptor 3 | Time Range Before Descriptor 3 Time Acceptable |
| | Time Range After Descriptor 3 Time Acceptable |
| | Instructions for Selecting Appropriate Record(s) |
| ⋮ | |
| Descriptor N | Time Range Before Descriptor N Time Acceptable |
| | Time Range After Descriptor N Time Acceptable |
| | Instructions for Selecting Appropriate Record(s) |

| List of Types of Records | |
|---|---|
| Record Type 1 | Temporal Descriptor Definition |
| ⋮ | |
| Record Type N | Temporal Descriptor Definition |

Figure 3

| Temporal Descriptor Definition | |
|---|---|
| Temporal Descriptors | Time Range & Instructions |
| Admission | Time Range Before Admission Time Acceptable |
| | Time Range After Admission Time Acceptable |
| | Instructions for Selecting Appropriate Record(s) |
| Discharge | Time Range Before Discharge Time Acceptable |
| | Time Range After Discharge Time Acceptable |
| | Instructions for Selecting Appropriate Record(s) |
| Descriptor 3 | Time Range Before Descriptor 3 Time Acceptable |
| | Time Range After Descriptor 3 Time Acceptable |
| | Instructions for Selecting Appropriate Record(s) |
| ⋮ | |
| Descriptor N | Time Range Before Descriptor N Time Acceptable |
| | Time Range After Descriptor N Time Acceptable |
| | Instructions for Selecting Appropriate Record(s) |

Figure 4

METHOD AND SYSTEM FOR RESOLVING TEMPORAL DESCRIPTORS OF DATA RECORDS IN A COMPUTER SYSTEM

RELATED APPLICATIONS

This application is a continuation in part of U.S. application Ser. No. 08/871,818, now U.S. Pat. No. 5,903,889 which was filed on Jun. 9, 1997 and issued on May 11, 1997, is entitled "System and Method for Translating, Collecting and Archiving Patient Records" and for which the inventor of the concepts in the present application is also an inventor.

This application claims priority from the applicant's co-pending provisional application Serial No. 60/054,923, filed Aug. 8, 1997.

FIELD OF THE INVENTION

The present invention relates generally to the field of data processing and more particularly to the field of automated data retrieval in a computer system.

BACKGROUND OF THE INVENTION

In a computerized data processing environment, the storage and retrieval of data records according to their time and date of creation has conventionally required detailed knowledge of those various dates and times by a system user who desires to locate, reference, or retrieve a particular data record. A well-known system in which this problem occurs is a hospital computer system which stores a variety of patient data records, many having been created at different dates and times. For example, when a patient is admitted to a hospital, a physician customarily writes an admission report. Similarly, upon the patient's discharge, a discharge report is written for the patient's file. These reports are typically recorded electronically as data records in a Hospital Information System (HIS) or a separate Admit, Discharge, and Transfer (ADT) System. In addition to these admission and discharge reports, there are often medical tests, observations, findings, or results regarding the patient under study, and all of these may be created at different dates and times.

Retrieving records created on a particular date or in conjunction with a particular event (e.g., the patient's admission to the hospital) is difficult, if not impossible, when there is no facility for identifying records with the date of creation or with an event with which the record is associated.

Moreover, data records are often of the same data type (e.g., electrocardiogram, or "ecg", report), but are recorded at different times throughout the duration of the patient's stay in the hospital. Thus, there is the additional problem of distinguishing among records of the same type which are created at different times. Identifying the earliest record of a particular type for a particular patient becomes an acute problem when file naming conventions do not allow for any identification of the time and date of record creation.

A further problem of record identification occurs when one patient report (or equivalently, the electronic record embodying the report) includes references to other reports on the same patient. Often, an admission report or similar report will be written to include direct references to other reports made on the patient. For example, an admission report will typically refer to reports that are made contemporaneously with the patient's admission to the hospital. An admission report may refer to the admission ecg or other types of reports commonly made at the time of admission. Similarly to admission reports, discharge reports and other report types often refer to medical information collected and recorded at various specific times. Examples include the "discharge ecg," the "admission ecg," the "previous discharge ecg," or some other ecg described by a temporal word or phrase (collectively, "temporal descriptors") that can convey to the reader when the ecg was recorded and, indirectly, the reason it was recorded.

To uniquely and unambiguously identify a particular report (data record) by reference, the physician typically would have to refer to it by the specific date and time it was made. For example, an ecg report made at the time of admission must be specifically referred to by the date and time of admission. This requires a level of detail beyond what is typically immediately available to a physician. Alternatively, a temporal descriptor may be employed to serve as a shorthand designation for a particular record.

For example, "admission ecg" may be used to refer to that report instead of the date and time of its creation. Likewise, "current," "admission, " "discharge" and "prior" are temporal descriptors which can uniquely identify a particular record from a group of records of the same type.

The use of such temporal descriptors can advantageously provide inherently greater meaning for the reader than the simple admission date and time. Such temporal descriptors are easily understood by medical staff or other reader. However, the use of these temporal descriptors in conjunction with computer systems that are used to store these records may lead to imprecision and uncertainty. Some types of records may be created several times during the day of admission or discharge, each being based on a separate set of observations. Thus, "admission ecg" may ambiguously refer to one or more of a number of ecg reports made on a patient at or near the time of his admission to the hospital. Accordingly, a selection must be made to accurately select the correct record or group of records from a set of the same type of records.

More particularly, and as a further example, an ecg may be recorded on a patient in the emergency room an hour before the patient was technically admitted into the hospital, yet this ecg may still be referred to as the "admission ecg" as opposed to one recorded 3 hours after the admission is officially recorded by the ADT system. In the case of a laboratory test there may be a requirement that to be called an admission laboratory test, that it must have been recorded within 2 hours of the time of admission. This is because values of such a test may change quickly and a value beyond the specified time range may not be relevant to the patient's condition upon admission. On the other hand, for a catheterization procedure, the requirement may be that it be recorded within 8 hours before or after the time of admission, as any catheterization procedure in that time range may be acceptable to be referred to as the admission catheterization.

It may also be desirable to take additional steps for specific types of records, for example, to give extra priority to records stored after the time of admission instead of those prior to the admission time in the case where more than one of the same type of record was stored within the allowed time range.

The foregoing use of temporal descriptors does not pose a significant problem for the human reader, who can interpret the temporal descriptors and locate the referenced record on his own. But, with the advent of interconnected computer systems storing a variety of records and with the advent of Internet/Intranet technologies with universal display, retrieval and interactive "browser" programs, it is now possible to create medical records that contain hyperlinks to various other stored records. By activating a hyperlink, a desired record is sought to be retrieved from a database server and sent to the requesting client terminal for display. To activate a hyperlink to records described by a temporal descriptor, there must be a means to select the record or group of records referred to by the temporal descriptor. This means should be capable of being executed at the time a record is retrieved, or alternatively soon after the time the report that contains the hyperlink to a record is created.

SUMMARY OF THE INVENTION

In accordance with the foregoing and other objects, there is provided a computer system characterized by one or more data record input devices, which may be workstations or data entry terminals that permit users to create data records and retrieve data records from the system. The computer system is further characterized by at least one database for storing data records entered by users of the system, and these databases may be physically separate from or integral with the workstations or terminals of the system.

There is further provided means interoperable with the workstations for creating data records that contain temporal descriptors of a predetermined character. These temporal descriptors are included within references to other records stored, or to be stored, on the system. The data record creation means comprises a processor and associated software governing the type and format of records to be created by the users and controlling the storage and retrieval of data records under the direction of the user.

The invention further provides means for selecting the data records referred to by the temporal descriptors from among a set of data records of the same type. The selecting means comprises a list of various record types stored on databases in the hospital. For each record type, there is provided an associated list of temporal descriptors which may be used to identify and refer to data records of that particular type. For each such temporal descriptor, there is specified one or more date and time ranges defining the limits of the creation dates and times of records called for by the temporal descriptor. There is also provided one or more instructions for selecting records when none of the existing data records satisfy the aforesaid date and time range.

BRIEF DESCRIPTION OF THE DRAWINGS

The present invention is more easily understood with reference to the drawings, in which:

FIG. 3 depicts a table containing a list of record types and temporal descriptor definitions associated with each record type.

FIG. 4 depicts a table containing time ranges and instructions contained within the temporal descriptor definitions of FIG. 3.

DETAILED DESCRIPTION OF THE PREFERRED EMBODIMENT

Figure 1:
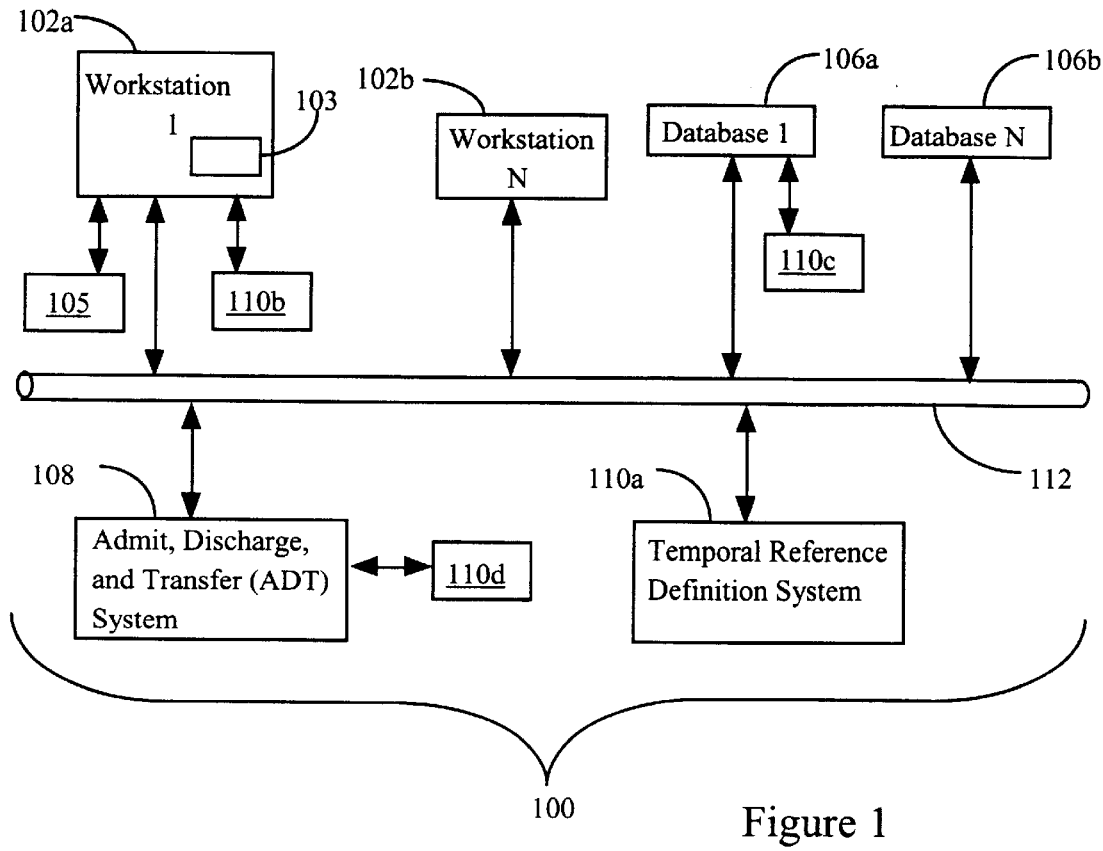
FIG. 1 is a block diagram of a computer system according to the present invention.

In the preferred embodiment, the computer system of the present invention comprises a medical computer network 100, as shown in FIG. 1. Medical computer network 100 comprises a plurality of computer workstations 102a, 102b which are preferably personal computers placed in a hospital, clinic or doctor's office. Workstations 102 are in communication with at least one of a plurality of databases 106a, 106b via network 112, which may be a combination of local and wide area networks, employing ETHERNET, serial line, or other communication protocols. Communication network 112 may also be arranged in such a manner as to be part of an Intranet or part of the well-known Internet. Each database 106a, 106b is provided for storing data records in structures defined by the operating characteristics of the database. Each database is preferably physically separate from a workstation 102a, 102b, although it will be understood that a database may be implemented as an integral part of a workstation, thus obviating the need for communication between workstation and database over network 112.

Each workstation 102a, 102b is preferably in communication with a data record creation means 105, which preferably comprises a word processing software program running on the workstation to permit users to create records containing temporal descriptors which refer to other data records stored on, or to be stored on, the computer system. Data record creation means 105 need not run on workstation 102a, as it may run on a server for one of the databases 106a, 106b, or any other processor in communication with the network 112 so as to allow a user to create data records from one of workstations 102a, 102b.

Also shown in FIG. 1, an Admit, Discharge, and Transfer (ADT) system 108 records the date and time when each patient is admitted to and discharged from the hospital. ADT system 108 preferably also records the location of the patient in the hospital as the patient is transferred from room to room, as well as the date and time of each such transfer. ADT system 108 may also record the date and time of specific medical procedures commenced and terminated at each location.

Each of the plurality of workstations 102a, 102b is preferably also running a universal display, retrieval, and interaction program, or "browser" 103. Browser 103 is capable of responding to an action by a user to send, via network 112, a request for additional information. Such action is referred to as exercising a hyperlink to the additional information.

Each data record containing a reference to other data records is formatted to contain hyperlinks to the referenced data records. Preferably, the creation of the hyperlinks is done automatically by data record creation means 105, which recognizes that a user has entered a date and report type (where the user knows the date and time of creation). Data record creation means 105 creates the hyperlink "on the fly" prior to the initial storage of the data record. Alternatively, the hyperlink may be constructed after initial storage of the data record by trained personnel who inspect the data record for references to other data records and construct suitable hyperlinks accordingly. This may be done with conventional word processing programs with hypertext markup language (HTML) capability, such as MICROSOFT WORD software, or it may be done with special-purpose HTML programs, such as Microsoft's FRONT PAGE package.

Figure 2A:
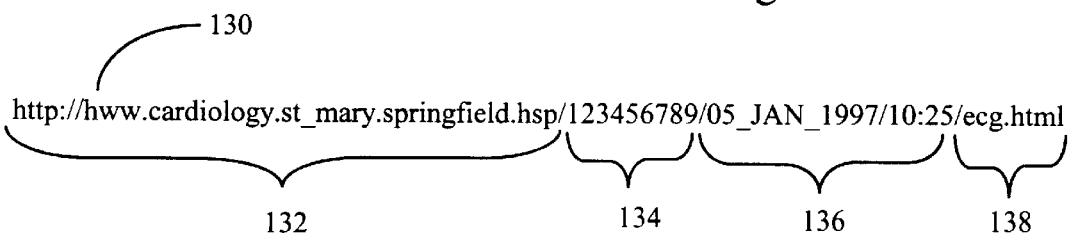
FIGS. 2A and 2B illustrate samples of hyperlink addresses used to retrieve records according to the present invention.

The hyperlink preferably includes an address that identifies a database 106a or 106b where the desired record is to be found. FIG. 2A depicts an exemplary specific hyperlink address 130 for retrieving a specific report type (here, an ecg) with a known date and time of creation. The database holding ecg records is identified by the address portion 132, which also identifies the transport method to be used, e.g., http (hyper text transfer protocol). Address portion 132 may be followed by an identification number 134 to identify a specific patient. The specific date and time 136 of the desired record is included, as is an indication of the specific type of record 138 (e.g., ecg) to be retrieved. In this example, a specific ordering of identifying information has been shown; however, other orderings may be used, or the request may be presented using a common gateway interface (cgi) request.

When hyperlink address 130 is received by the database 106*a* targeted by the address, the designated record is retrieved if it is available. If one is available, database 106*a* may format the ecg record and send it to the requesting workstation 102*a* for display. If no such record is available, a message may instead be sent to workstation 102*a* indicating that no such record is available. In this case, a list of other records near the date and time specified may be presented for the user to choose from.

Figure 2B:
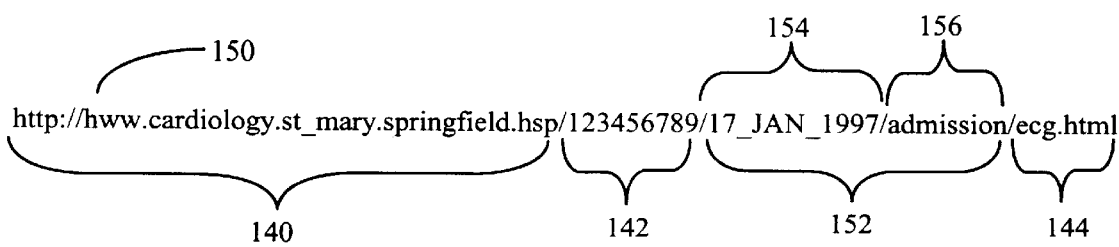

If the date and time of creation of a data record are not known to the user, then temporal descriptors must be used when creating reports that refer to other reports, or when requesting a particular report. In this preferred embodiment, data record creation means 105, having recognized a temporal descriptor in a data record being created, constructs a hyperlink such as that shown in FIG. 2B. For example, to retrieve an ecg referred to by a specific request or in a data record as an "admission ecg,") temporal hyperlink address 150 may be used. Database address 140, patient identification number 142, and record type 144 are analogous to their corresponding components of specific hyperlink address 130 in FIG. 2A. However, the record to be retrieved is now specified by temporal date 152, which comprises date 154 and temporal descriptor 156. Date 154 is typically the date when the report incorporating the temporal hyperlink 150 was created. In the present example, the time of report creation has not been included, but may be included if desired.

Preferably, the foregoing hyperlink is sent to the database identified by address 140, which resolves the temporal descriptor, as will now be described. This is done as follows. When temporal hyperlink address 150 is received by the appropriate database 106, the meaning of the temporal date 152 must be resolved before a record can be located for retrieval. Using date 154, database 106 may send a request to the ADT system 108 for the date and time corresponding to the activity specified by temporal phrase 156 prior to date 154 for the patient specified by identification number 142. ADT system 108 will respond with the date and time of the most recent activity specified by temporal descriptor 156 (if any) prior to date 154.

Database 106*a* may then send a request to Temporal Reference Definition System (TRDS) 110*a* to determine the allowable range of times for type of record 144 that may be considered to be associated with temporal descriptor 156. TRDS 110*a* selects the desired data records according to definitions corresponding to the record type, as shown in FIG. 3. TRDS 110*a* comprises a table 170 of record types 172 and associated temporal descriptor definitions 174, and there may be different definitions associated with each record type. It will be understood that such a definition system may be in direct communication with a workstation 102*a* or 102*b*, database 106*a* or 106*b*, or ADT system 108 (shown as 110*b*, 110*c*, and 110*d*, respectively, in FIG. 1) rather than over the network 112.

The contents of temporal descriptor definitions 174 is shown in FIG. 4. For each temporal descriptor 202, there is a corresponding entry defining the time range and instructions 204. A search of temporal phrases 202 is made to find one that corresponds to the temporal descriptor 156 (FIG. 2B) used to identify the record to be retrieved. When a match is found, the corresponding entry defining the time range and instructions 204 are returned to requesting database 106. Time range and instructions 204 preferably include acceptable times 210 before the event specified by temporal descriptor 202 and acceptable times 212 after that event. It may also include instructions 214 such as weighting procedures; for example, those that favor records found after the occurrence of the temporal descriptor event. These weighting procedures may include programming codes, such as using the Java language, to be used by database 106*a* to select the correct record.

Database 106*a* preferably now retrieves all of the records of the specific type of record 144 which are for the specified patient corresponding to identification number 142. Next, database 106*a* preferably compares the dates and times of those retrieved records to find those that meet the time range specified by time range and instructions 204 for the specified temporal descriptor definition 174 for type of record 144 selected.

Further, time range and instructions 204 may be used to select one record if several records are within the time ranges specified. Database 106*a* may now format as required and transmit the record to workstation 102*a* requesting the record for display.

In an alternative embodiment, a different means may be employed to assist in the retrieval of the correct record corresponding to a temporal descriptor. Prior to or soon after storing each record, a temporal notation corresponding to a particular temporal descriptor may be made in the record, and this temporal notation, or "tag," can thereafter be located by the corresponding database 106 used to store this type of record. In this manner of "tagging" each record, the database may only need to determine which record has been tagged for the matching temporal descriptor prior to a date specified by the retrieval request.

The foregoing embodiments use record type listing 170 and temporal phrase definition 174 information to select a record when a report is stored in a database. In that case, prior to storage or soon thereafter, any hyperlinks that contain temporal dates 152 are converted to hyperlink addresses by locating the specific date and time of the record that corresponds to a temporal date. However, the same techniques may also be employed to retrieve a data record on demand by a user who merely enters a request at workstation 102*a*, where such request includes a record type and associated temporal phrase. In this manner, the present invention is not limited to the use of references within data records, but may be extended to database queries entered spontaneously by a user of the system.

While a particular embodiment of the invention has been illustrated and described, it will be obvious to those skilled in the art that various changes and modifications may be made without sacrificing the advantages provided by the principles of operation disclosed herein.

I claim:

1. A computer system for automated retrieval and referencing of data records using temporal descriptors, comprising:

a data record input device capable of receiving a temporal descriptor from a user of the device;

a database in communication with said data record input device for storing data records referred to by said temporal descriptor;

means for creating a first data record, means, upon creating the first data record, identifying the date of creation of the first data record, said means operable to construct a hyperlink to other data records from said temporal descriptor and the date of creation of said data record; and means associated with the database for selecting at least one data record from a group of data records stored on the database, said selection being based at least in part upon the temporal descriptor and the date of creation of said first data record.

2. The computer system of claim 1, wherein said hyperlink further comprises a data record type for use in selecting a particular type of data record from said group of data records.

3. The computer system of claim 1, wherein said selection means comprises a plurality of time ranges corresponding to a plurality of temporal descriptors, each of said time ranges defining time limits before and after an event associated with the corresponding temporal descriptor.

4. The computer system of claim 3, wherein said hyperlink further comprises a data record type for use in selecting a particular type of data record from said group of data records.

5. The computer system of claim 3, wherein said selection means further comprises instructions corresponding to each temporal descriptor for making a further selection of data records from those data records within said time limits for a corresponding temporal descriptor.

6. The computer system of claim 5, wherein said hyperlink further comprises a data record type for use in selecting a particular type of data record from said group of data records.

7. The computer system of claim 6, wherein said data records are patient records and said computer system is a hospital computer system.

8. A method for automatically retrieving data records in a computer system, comprising:

receiving a temporal descriptor entered by a user of the computer system;

recognizing said temporal descriptor with a word processor;

creating a first data record including said temporal descriptor identifying the date of creation of the first data record;

creating a hyperlink comprising said temporal descriptor and the date of creation of said first data record;

selecting at least one other data record from a group of data records stored on a database on said computer system, said selection being made using the temporal descriptor and the date of creation; and retrieving said at least one other data record for displaying to said user.

9. The method of claim 8, wherein said hyperlink further comprises a data record type and said selection is made using the data record type to select a particular type of data record from said group of data records.

10. The method of claim 8, further comprising associating said temporal descriptor with a time range defining time limits before and after an event associated with said temporal descriptor.

11. The method of claim 10, wherein said hyperlink further comprises a data record type and said selection is made using the data record type to select a particular type of data record from said group of data records.

12. The method of claim 10, wherein the selecting step further comprises using a list of instructions associated with said temporal descriptor to further select data records from those data records within said time limits.

13. The method of claim 12, wherein said hyperlink further comprises a data record type and said selection is made using the data record type to select a particular type of data record from said group of data records.

14. The method of claim 13, wherein said hyperlink is created automatically by a word processor.

15. The method of claim 14, wherein said data records are patient records and said computer system is a hospital computer system.

16. A computer system for automated retrieval and referencing of data records from among a plurality of data records in a database, comprising:

means for constructing a hyperlink including a database address, a temporal date and a data record type;

means for making a temporal notation in a data record stored in said database, said temporal notation corresponding to a second temporal descriptor;

said temporal date including a date and a temporal descriptor, said temporal descriptor corresponding to a time range and instructions, said time range and instructions used to select at least one data record created prior to said date.

17. The computer system of claim 16, wherein said plurality of data records comprises a plurality of data record types, each of said data record types having a temporal descriptor definition table defined therefor, and said temporal descriptor table defining separate time ranges and instructions for each of a plurality of temporal descriptors.

18. The computer system of claim 16, wherein said hyperlink address includes patient identification information for selecting data records relating to a patient.

19. The computer system of claim 16, wherein said hyperlink forms part of a data record.

20. The computer system of claim 19, wherein said hyperlink address includes patient identification information for selecting data records relating to a patient.

21. The computer system of claim 19, wherein said hyperlink construction means is operable to construct said hyperlink as part of a data record.

22. The computer system of claim 21, wherein said hyperlink address includes patient identification information for selecting data records relating to a patient.

23. A method for automated retrieval and referencing of data records from among a plurality of data records in a database, comprising:

constructing a hyperlink including a database address, a temporal date and a data record type, said temporal date including a date and a first temporal descriptor, making a temporal notation in a data record stored in said database, said temporal notation corresponding to a second temporal descriptor, using said first temporal descriptor to select a first data record in said database by match between said first and second temporal descriptor, said first data record being created prior to said date, retrieving said first data record from said database.

24. The method of claim 23, wherein said hyperlink address includes patient identification information for selecting data records relating to a patient.

25. The method of claim 23, wherein said hyperlink forms part of a data record.

26. The method of claim 25, wherein said hyperlink address includes patient identification information for selecting data records relating to a patient.

27. The method of claim 25, wherein said hyperlink construction means is operable to construct said hyperlink as part of a data record.

28. The method of claim 27, wherein said hyperlink address includes patient identification information for selecting data records relating to a patient.

29. A computer system for automated retrieval and referencing of data records using temporal descriptors, comprising:
   a data record input device capable of receiving a temporal descriptor from a user of the device;
   a processor for creating a first data record, said processor operable to construct a hyperlink to other data records from said temporal descriptor and the date of creation of said data record;
   a database in communication with said data record input device for storing data records referred to by said temporal descriptor, the database also selecting at least one data record from a group of data records stored on the database, said selection being based at least in part upon the temporal descriptor and the date of creation of said first data record.

30. The computer system of claim 29, wherein said hyperlink further comprises a data record type for use in selecting a particular type of data record from said group of data records.

31. The computer system of claim 29, wherein the database includes a temporal descriptor definition table including a plurality of time ranges corresponding to a plurality of temporal descriptors, each of said time ranges defining time limits before and after an event associated with the corresponding temporal descriptor.

32. The computer system of claim 30, wherein the descriptor definition table further comprises instructions corresponding to each temporal descriptor for making a further selection of data records from those data records within said time limits for a corresponding temporal descriptor.

33. The computer system of claim 32, wherein said hyperlink further comprises a data record type for use in selecting a particular type of data record from said group of data records.

34. The computer system of claim 33, wherein said data records are patient records and said computer system is a hospital computer system.

35. A computer system for automated retrieval and referencing of data records from among a plurality of data records in a database, comprising:
   a processor for constructing a hyperlink including a database address, a temporal date and a data record type;
   said temporal date including a date and a temporal descriptor, said temporal descriptor corresponding to a time range and instructions, said time range and instructions used to select at least one data record created prior to said date.

36. The computer system of claim 35, wherein said plurality of data records comprises a plurality of data record types, each of said data record types having a temporal descriptor definition table defined therefor, and said temporal descriptor table defining separate time ranges and instructions for each of a plurality of temporal descriptors.

37. The computer system of claim 35, wherein said hyperlink address includes patient identification information for selecting data records relating to a patient.

38. The computer system of claim 35, wherein said hyperlink forms part of a data record.

39. The computer system of claim 38, wherein said hyperlink address includes patient identification information for selecting data records relating to a patient.

40. The computer system of claim 38, wherein said hyperlink construction means is operable to construct said hyperlink as part of a data record.

41. The computer system of claim 40, wherein said hyperlink address includes patient identification information for selecting data records relating to a patient.

42. A computer system for automated retrieval and referencing of data records from among a plurality of data records in a database, comprising:
   a processor running a pulse sequencing program to perform the steps of:
      (a) constructing a hyperlink including a database address, a temporal date and a data record type, said temporal date including a date and a first temporal descriptor,
      (b) making a temporal notation in a data record stored in said database, said temporal notation corresponding to a second temporal descriptor,
      (c) using said first temporal descriptor to select a first data record in said database by match between said first and second temporal descriptor, said first data record being created prior to said date; and
      (d) retrieving said first data record from said database.

43. The system of claim 42, wherein said hyperlink address includes patient identification information for selecting data records relating to a patient.

44. The system of claim 42, wherein said hyperlink forms part of a data record.

45. The system of claim 44, wherein said hyperlink address includes patient identification information for selecting data records relating to a patient.

46. The system of claim 44, wherein said hyperlink construction means is operable to construct said hyperlink as part of a data record.

47. The system of claim 46, wherein said hyperlink address includes patient identification information for selecting data records relating to a patient.

48. A method for use with a computer system for automated retrieval and referencing of data records from among a plurality of data records in a database, the method comprising the steps of:
   constructing a hyperlink including a database address, a temporal date and a data record type, said temporal date including a date and a temporal descriptor, said temporal descriptor corresponding to a time range and instructions, said time range and instructions useable to select at least one data record created prior to said date.

49. The method of claim 48, wherein said plurality of data records comprises a plurality of data record types, each of said data record types having a temporal descriptor definition table defined therefor, and said temporal descriptor table defining separate time ranges and instructions for each of a plurality of temporal descriptors.

50. The method of claim 48, wherein said hyperlink address includes patient identification information for selecting data records relating to a patient.

51. The method of claim 48, wherein said hyperlink forms part of a data record.

52. The method of claim 51, wherein said hyperlink address includes patient identification information for selecting data records relating to a patient.

53. The computer system of claim 51, wherein said hyperlink address includes patient identification information for selecting data records relating to a patient.

* * * * *